(12) United States Patent
Tanaka et al.

(10) Patent No.: US 10,995,315 B2
(45) Date of Patent: May 4, 2021

(54) ALGAE SEPARATING DEVICE AND METHOD FOR PRODUCING DRY ALGAE

(71) Applicant: IHI CORPORATION, Tokyo (JP)

(72) Inventors: Hiroshi Tanaka, Tokyo (JP); Jun Muto, Tokyo (JP); Yoshiaki Matsuzawa, Tokyo (JP); Norimitsu Kaneko, Tokyo (JP); Yuko Yoshida, Tokyo (JP)

(73) Assignee: IHI CORPORATION, Tokyo (JP)

( * ) Notice: Subject to any disclaimer, the term of this patent is extended or adjusted under 35 U.S.C. 154(b) by 412 days.

(21) Appl. No.: 15/816,039

(22) Filed: Nov. 17, 2017

(65) Prior Publication Data

US 2018/0072984 A1 Mar. 15, 2018

Related U.S. Application Data

(63) Continuation of application No. PCT/JP2016/064910, filed on May 19, 2016.

(30) Foreign Application Priority Data

May 20, 2015 (JP) ................. 2015-102909

(51) Int. Cl.
*C12N 1/12* (2006.01)
*B01D 24/38* (2006.01)
(Continued)

(52) U.S. Cl.
CPC ............... *C12N 1/12* (2013.01); *B01D 24/38* (2013.01); *B01D 29/00* (2013.01); *B01D 29/014* (2013.01); *B01D 29/88* (2013.01); *B01D 29/908* (2013.01); *B01D 39/10* (2013.01); *C12M 47/02* (2013.01); *C12N 1/02* (2013.01)

(58) Field of Classification Search
CPC ........ B01D 29/88; B01D 24/38; B01D 29/00; B01D 39/10; B01D 29/908; B01D 29/014; C12N 1/12; C12N 1/02; C12M 47/02
See application file for complete search history.

(56) References Cited

U.S. PATENT DOCUMENTS

| 5,593,579 | A | 1/1997 | Reynolds |
| 2010/0314323 | A1 | 12/2010 | Lean et al. |
| 2013/0319949 | A1 | 12/2013 | Booth et al. |

FOREIGN PATENT DOCUMENTS

| CN | 103517746 A | 1/2014 |
| JP | H04-118032 A | 4/1992 |

(Continued)

OTHER PUBLICATIONS

C. Stewart Slater et al., "Shear-enhanced microfiltration of microalgae in a vibrating membrane module," Clean Technologies and Environmental Policy, vol. 17, No. 7, Jan. 25, 2015, pp. 1743-1755, Springer Berlin Heidelberg, Berlin/Heidelberg, XP035534962, ISSN: 1618-954X, DOI: 10.1007/S10098-015-0907-Z.

*Primary Examiner* — Waqaas Ali (57) ABSTRACT

The present disclosure is an algae separating device configured to separate algae from an algal solution in which algae are suspended. The algae separating device includes: a metal screen having a main body and a plurality of through holes passing through the main body from a front face to a back face; and a spraying device configured to spray the algal solution toward the front face of the main body.

4 Claims, 5 Drawing Sheets

(51) Int. Cl.
*B01D 29/88* (2006.01)
*B01D 29/01* (2006.01)
*B01D 39/10* (2006.01)
*C12M 1/00* (2006.01)
*C12M 1/02* (2006.01)
*B01D 29/00* (2006.01)
*B01D 29/90* (2006.01)
*C12N 1/02* (2006.01)

(56) References Cited

FOREIGN PATENT DOCUMENTS

| | | |
|---|---|---|
| JP | 2004-066175 A | 3/2004 |
| JP | 2004-223361 A | 8/2004 |
| JP | 2006-150240 A | 6/2006 |
| JP | 2012-085539 A | 5/2012 |
| JP | 2012-179586 A | 9/2012 |
| JP | 2012-183002 A | 9/2012 |
| JP | 2013-027353 A | 2/2013 |
| JP | 2013-027378 A | 2/2013 |
| JP | 2014-168415 A | 9/2014 |
| KR | 100369677 B1 * | 1/2003 |
| WO | 1998/028082 A1 | 7/1998 |
| WO | 2012/039466 A1 | 3/2012 |
| WO | 2014/008203 A2 | 1/2014 |

* cited by examiner

ALGAE SEPARATING DEVICE AND METHOD FOR PRODUCING DRY ALGAE

CROSS-REFERENCE TO RELATED APPLICATIONS

The present application is a continuation application of International Application No. PCT/JP2016/064910, filed May 19, 2016, which claims priority to Japanese Patent Application No. 2015-102909, filed May 20, 2015. The contents of these applications are incorporated herein by reference in their entirety.

TECHNICAL FIELD

In recent years, attention has been paid to algae (particularly, microalgae) from which biofuels (hydrocarbons or biodiesels), physiologically active substances, or the like can be produced. In addition, extracting fuels, physiologically active substances, or the like from such algae or using such algae themselves for foods, medicines, cosmetics, or the like has been studied.

In order to take out fuels or the like from algae or use algae themselves for foods or the like, it is necessary to cultivate a large amount of algae in a culture device, separate the cultivated algae from the culture liquid, dry the algae themselves, and obtain a dry material (hereinafter referred to as "dry algae").

As a technique for separating algae from a culture liquid, a technique for filtering algae using a plankton net or centrifuging algae using a centrifugal separator (for example, Patent Document 1) or a technique for performing coagulation and sedimentation on algae by adding a coagulant to a culture liquid in which algae are suspended (for example, Patent Document 2) has been developed. Such techniques are also disclosed in Patent Documents 3 to 5.

DOCUMENTS OF THE RELATED ART

Patent Document

[Patent Document 1]
Japanese Unexamined Patent Application, First Publication No. 2012-183002
[Patent Document 2]
Japanese Unexamined Patent Application, First Publication No. 2012-179586
[Patent Document 3]
Japanese Unexamined Patent Application, First Publication No. 2013-027378
[Patent Document 4]
PCT International Publication No. WO2012/039466
[Patent Document 5]
Japanese Unexamined Patent Application, First Publication No. 2004-223361

SUMMARY

However, since a plankton net itself is formed of a resin such nylon, the plankton net is easily damaged due to low durability and thus maintenance costs therefor are incurred. A cost of centrifugal separator itself is high and running costs therefor are incurred. Furthermore, in a technique using a coagulant, the cost of the coagulant itself is high and a process of removing the coagulant is required. Therefore, development of a technique capable of separating out algae at low cost is required.

The present disclosure was made in view of the above-described circumstances, an objective thereof being to provide an algae separating device and a method for producing dry algae capable of separating out algae at low cost.

The present disclosure adopts the following constitution as means for solving the above-described objective. A first aspect of the present disclosure is an algae separating device configured to separate algae from an algal solution in which algae are suspended, the algae separating device including: a metal screen including a main body and a plurality of through holes passing through the main body from a front face to a back face; and a spraying device configured to spray the algal solution toward the front face of the main body.

A second aspect of the present disclosure is a method for producing dry algae which separates algae from an algal solution in which algae are suspended and produces dry algae, the method for producing the dry algae including: a step of spraying the algal solution toward a front face of a main body of a metal screen having the main body and a plurality of through holes passing through the main body from the front face to a back face.

According to the present disclosure, algae can be separated out at low cost.

DETAILED DESCRIPTION

Embodiments of the present disclosure will be described in detail with reference to the following drawings. Dimensions, materials, other specific numerical values, and the like illustrated in an embodiment are merely examples for facilitating the understanding of the present disclosure and do not limit the present disclosure unless otherwise mentioned. Note that, in the present specification and the drawings, constituent elements having substantially the same function and constitution will be denoted with the same reference numerals, repeated descriptions thereof will be omitted, and constituent elements which are not directly associated with the present disclosure will not be shown.

(Algae Separating Device 100)

In an embodiment, an algae separating device 100 configured to separate algae from an algal solution in which algae are suspended, dry the separated algae, and produce dry algae will be described. Note that *Botryococcus braunii* will be described as an example of algae. Furthermore, *Botryococcus braunii* may be a wild type strain and may be a mutant strain, a particle size of which is enlarged by inducing genetic modification or mutation.

Figure 1:
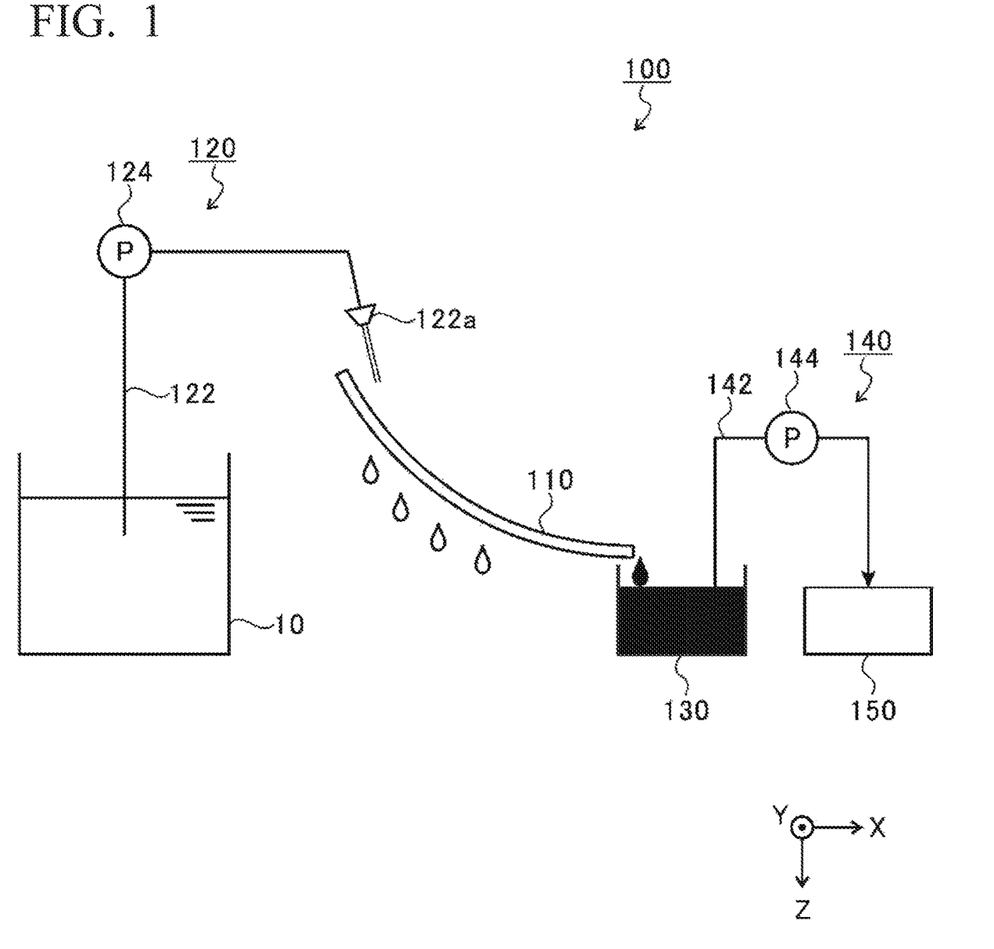
FIG. 1 is a diagram for describing an algae separating device.

FIG. 1 is a diagram for describing the algae separating device 100 according to the embodiment. Note that, in the embodiment, in FIGS. 1, 2A, 2B, and 3, an X axis (a horizontal direction), a Y axis (a horizontal direction), and a Z axis (a vertical direction) intersecting perpendicularly are defined as shown in the drawings. As shown in FIG. 1, the algae separating device 100 includes a screen 110, a spraying device 120, a collecting tank 130, a delivery device 140, and a drying device 150.

Figure 2A:
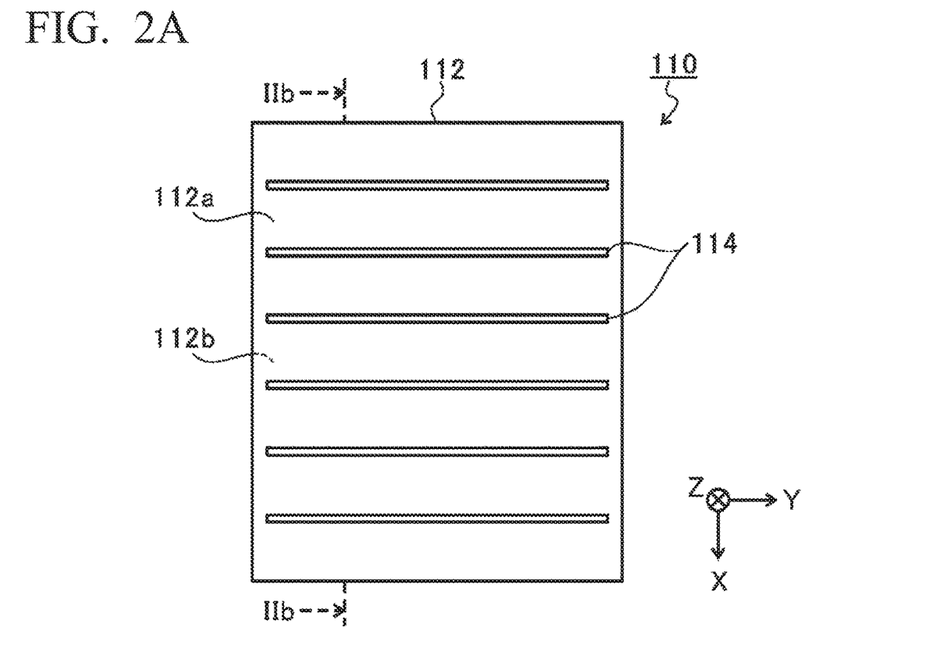
FIG. 2A is a diagram for describing a specific constitution of a screen.
Figure 2B:
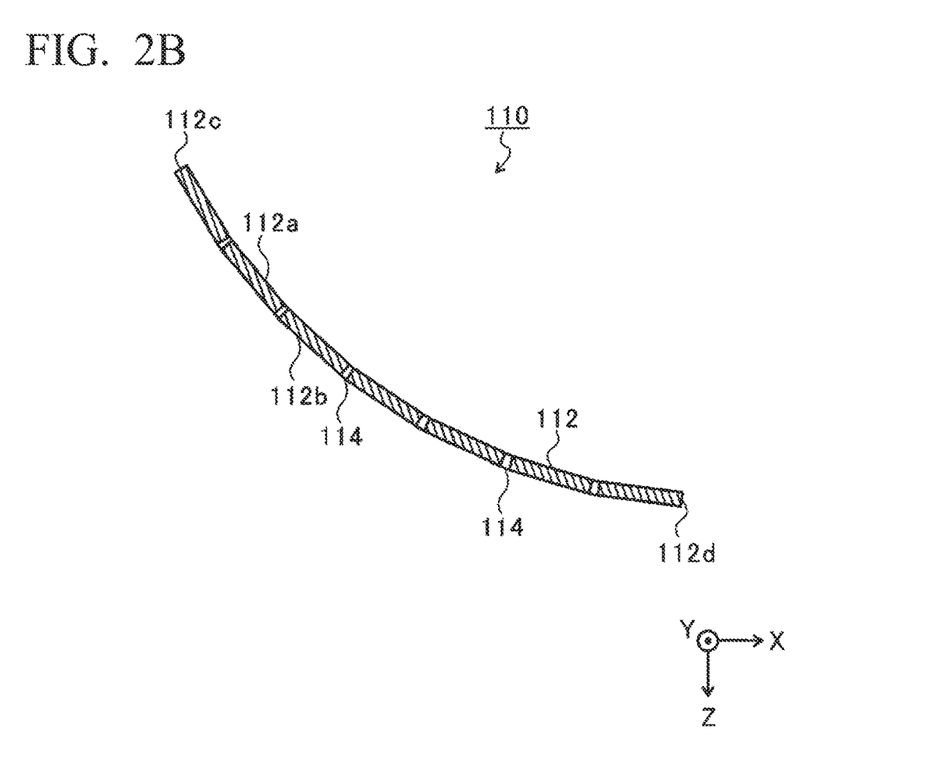
FIG. 2B is a diagram for describing a specific constitution of a screen.

The screen 110 removes a part of a liquid from an algal solution. FIGS. 2A and 2B are diagrams for describing a specific constitution of the screen 110, FIG. 2A is a plan view of the screen 110, and FIG. 2B is a cross-sectional view taken along line IIb-IIb in FIG. 2A. Note that, in FIGS. 2A and 2B, slits 114 are illustrated to be larger than the actual size thereof to facilitate the understanding of a reader.

As shown in FIGS. 2A and 2B, the screen 110 is constituted of a metal such as stainless steel and includes a plate-shaped main body 112. As shown in FIG. 2B, in the screen 110, one end side 112c of the main body 112 is arranged vertically (a Z axis direction in FIG. 2B) above the other end side 112d thereof.

The main body 112 is formed in a curved shape in which a front face 112a side is concave and a back face 112b side is convex and includes the plurality of slits 114 (through holes) passing from the front face 112a to the back face 112b and formed to extend in a Y axis direction of FIGS. 2A and 2B. Furthermore, a width of each of the slits 114 in an X axis direction of FIGS. 2A and 2B is set to a size less than a minimum particle size of algae. The width of the slit 114 is set to a size less than the minimum particle size of the algae so that the algae can be prevented from passing through the slit 114 and thus a reduction in collection efficiency of algae can be prevented. Note that, since a minimum particle size of algae can be measured using an existing particle size measuring device such as a particle size distribution analyzer, detailed description thereof will be omitted. Furthermore, when algae form a colony, the width of the slit 114 may be set to a size less than a minimum particle size of the colony.

Referring back to FIG. 1, the spraying device 120 includes a nozzle 122a, a pipe 122 having one end immersed in an algal solution stored in a culture tank 10 and the other end connected to the nozzle 122a, and a pump 124 provided in the pipe 122, suctions an algal solution from the culture tank 10, and sprays the suctioned algal solution to the screen 110. The nozzle 122a has a tapered shape in which a path cross-sectional area thereof gradually decreases from a proximal end connected to the pipe 122 toward a distal end thereof.

Figure 3:
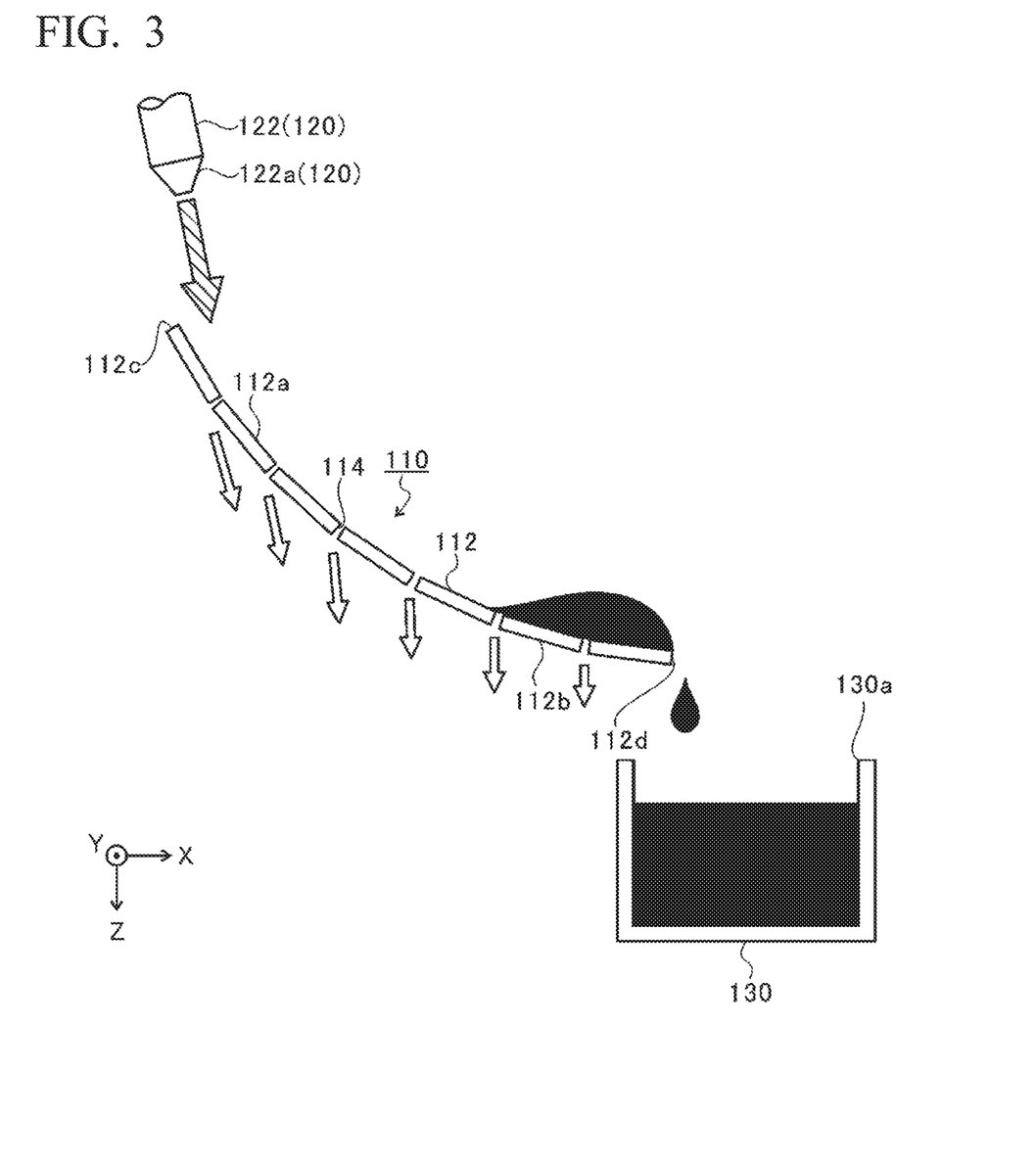
FIG. 3 is a diagram for describing a spraying state of an algal solution using a spraying device.

FIG. 3 is a diagram for describing a spraying state of an algal solution using the spraying device 120. In FIG. 3, as indicated by a hatched arrow, the spraying device 120 sprays an algal solution toward the front face 112a of the main body 112 of the screen 110. Thus, part of a liquid (a culture liquid or the like) of an algal solution passes through the slits 114 and falls below the screen 110 (indicated by outlined arrows in FIG. 3), and an algal solution from which some liquid has been removed (illustrated as a black object in FIG. 3; hereinafter referred to as a "concentrated algal solution") remains on the front face 112a of the main body 112. Furthermore, the spraying device 120 can spray an algal solution to efficiently pass a liquid through the slits 114 due to a spray pressure, and thus water removal efficiency of the algal solution (efficiency of removing a liquid from the algal solution) can be improved.

Also, in the embodiment, a spray direction of an algal solution using the spraying device 120 corresponds to a direction intersecting a plane direction of at least part of the front face 112a of the main body 112 and a direction intersecting at least one normal line of the main body 112. In other words, the spraying device 120 sprays an algal solution in a direction from the one end side 112c toward the other end side 112d. Thus, the concentrated algal solution moves in the direction from the one end side 112c toward the other end side 112d due to an impact when the algal solution is sprayed onto the front face 112a. Moreover, since the one end side 112c of the main body 112 of the screen 110 is arranged vertically above the other end side 112d as described above, it is also possible for the concentrated algal solution to move from the one end side 112c to the other end side 112d using its own weight. Therefore, it is unnecessary to use a dedicated power for moving the concentrated algal solution, and thus it is possible to reduce the costs required for power.

As described above, in a process in which the concentrated algal solution moves from the one end side 112c to the other end side 112d, a liquid is gradually removed from the concentrated algal solution through the plurality of slits 114. Thus, a degree of concentration of the concentrated algal solution (a concentration of algae in the concentrated algal solution) can be gradually increased as the concentrated algal solution moves from the one end side 112c to the other end side 112d. Moreover, the concentrated algal solution which has reached the other end side 112d falls due to its own weight and is accommodated in the collecting tank 130.

The collecting tank 130 includes an upper opening 130a disposed above the other end side 112d of the main body 112 and open toward the other end side 112d and accommodates the concentrated algal solution.

Referring again to FIG. 1, a delivery device 140 has a pipe 142 having one end immersed in the concentrated algal solution stored in the collecting tank 130 and the other end connected to the drying device 150 and a pump 144 provided in the pipe 142 and sends the concentrated algal solution to the drying device 150.

The drying device 150 dries the concentrated algal solution obtained through concentration associated with the screen 110 using natural drying (sun drying, drying in shade, or the like) and produces dry algae. Natural drying may be used for the drying device 150 so that it is possible to reduce the costs required for drying. The dry algae produced in this way are processed into a fuel through solvent extraction treatment or the like.

As described above, according to the algae separating device 100 of the embodiment, algae can be separated from an algal solution (by concentrating the algal solution) with a simple constitution of spraying the algal solution from the spraying device 120 toward the metal screen 110. Therefore, it is possible to separate algae out at low cost in comparison to a technique using a centrifugal separator with a technique using a coagulant. Furthermore, since there is no need to use a device with high running costs, the running costs can be reduced as compared to a technique using a centrifugal separator. Since addition of additives such as a coagulant is not required, a process of removing the additives is not required in contrast to a technique using a coagulant. In addition, since the metal screen 110 is used, durability can be improved as compared to a technique using a resin plankton net. Thus, the maintenance costs thereof can be reduced.

(Method for Producing Dry Algae)

Figure 4:
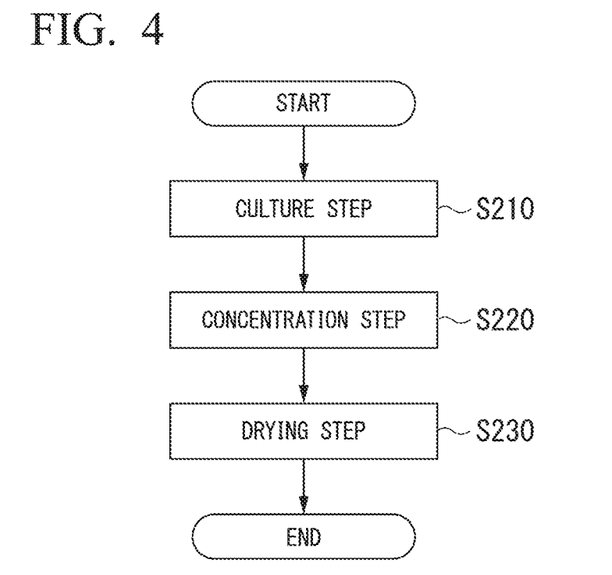
FIG. 4 is a flowchart for describing a flow of a process of a method for producing dry algae.

Next, a method for producing dry algae using the algae separating device 100 will be described. FIG. 4 is a flowchart for describing a flow of a process of the method for producing dry algae according to the embodiment.

As shown in FIG. 4, as a first step, a culture liquid and algae are accommodated in the culture tank 10, carbon dioxide is introduced (aerated) therein, and algae are cultivated (a culture step: S210). As a second step, the spraying device 120 of the algae separating device 100 suctions an algal solution from the culture tank 10 and sprays the suctioned algal solution to the front face 112a of the main body 112 of the screen 110 (a concentration step: S220). Thus, part of a liquid in the algal solution is removed using the screen 110, concentrated algal solution is generated, and the concentrated algal solution obtained through concentration associated with the screen 110 is accommodated in the collecting tank 130. As a third step, the delivery device 140 sends the concentrated algal solution from the collecting tank 130 to the drying device 150 and the drying device 150 dries the concentrated algal solution to produce dry algae (a drying step: S230).

As described above, according to the method for producing the dry algae of the embodiment, dry algae can be produced at low cost and thus the costs of products such as a fuel produced from dry algae can be reduced.

Modified Example

Figure 5A:
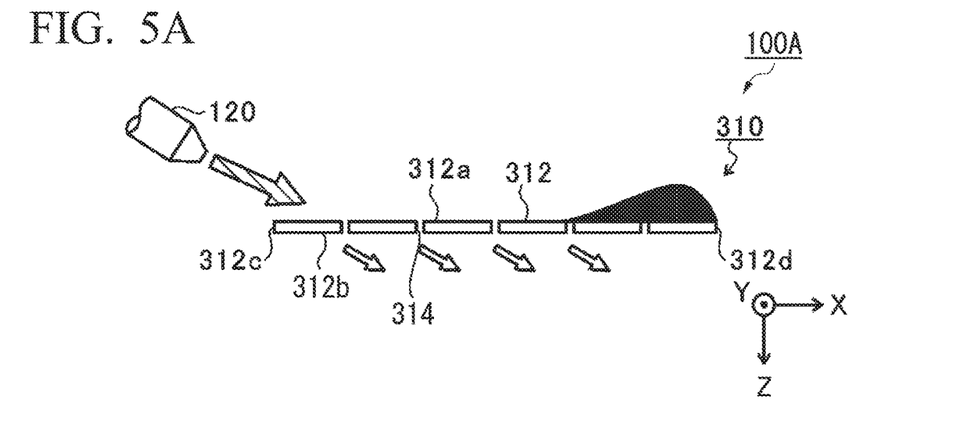
FIG. 5A is a diagram for describing a modified example of the algae separating device.
Figure 5B:
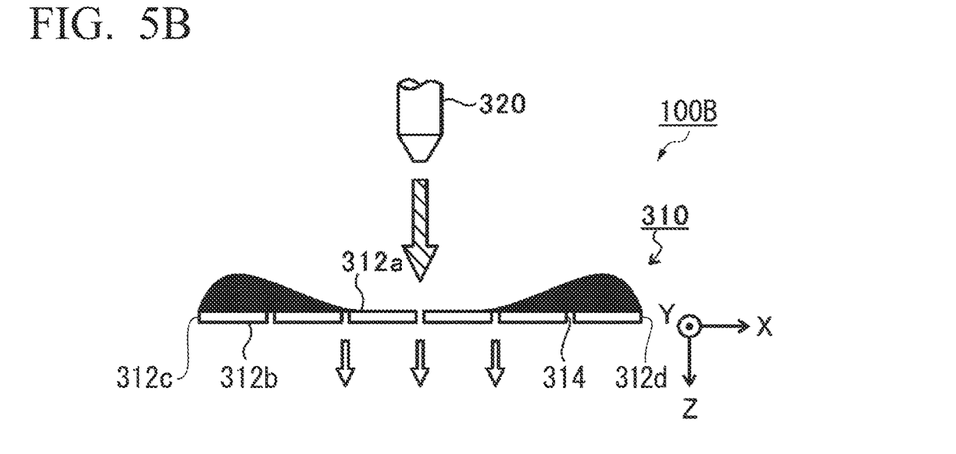
FIG. 5B is a diagram for describing a modified example of the algae separating device.
Figure 5C:
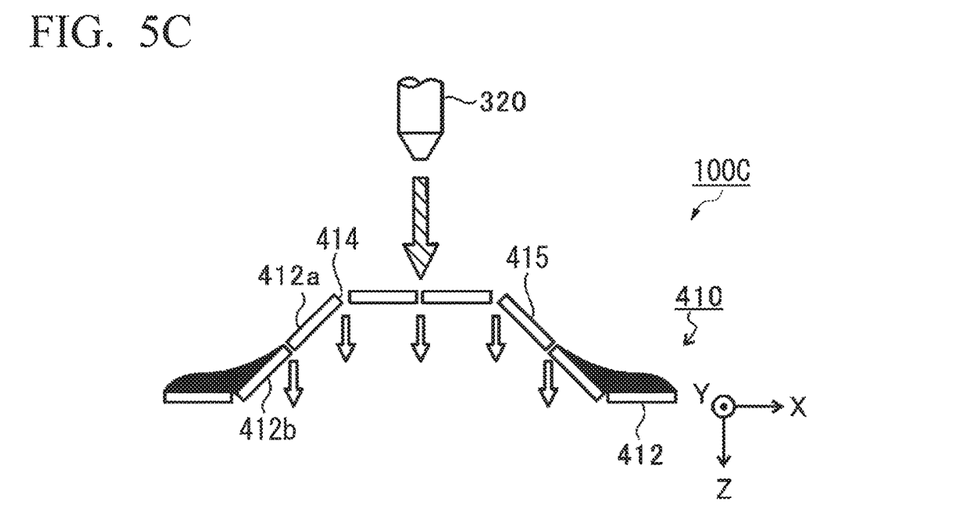
FIG. 5C is a diagram for describing a modified example of the algae separating device.

FIGS. 5A to 5C are diagrams for describing algae separating devices 100A, 100B, and 100C which are modified examples of the algae separating device 100 according to the above-described embodiment. In FIGS. 5A to 5C, parts of screens and spraying devices are illustrated to facilitate the understanding of the reader. Moreover, also in FIGS. 5A to 5C, like in FIG. 3, an algal solution is indicated by a hatched arrow, a liquid passing through slits is indicated by outlined arrows, and the concentrated algal solution is illustrated as a black object.

In the above-described embodiment, the screen 110 in which the one end side 112c of the main body 112 is arranged vertically above the other end side 112d has been described as an example. However, one end side of a main body in a screen may not be arranged vertically above the other end side thereof, and as shown in FIG. 5A, the algae separating device 100A may adopt a screen 310, a main body 312 of which extends in a horizontal direction (an X direction and a Y direction of FIG. 5). Note that, even when such a screen 310 is adopted, a spray direction of an algal solution associated with the spraying device 120 corresponds to a direction intersecting a plane direction of at least part of a front face 312a of the main body 312 and a direction from one end side 312c toward the other end side 312d. An algal solution is sprayed in such a direction so that the concentrated algal solution can move to the other end side 312d side and thus the concentrated algal solution can be easily collected. To be specific, in a process in which the concentrated algal solution moves from the one end side 312c to the other end side 312d, a liquid is gradually removed from the concentrated algal solution from the front face 312a of a screen 310 toward a back face 312b thereof through a plurality of slits 314. Thus, a degree of concentration of the concentrated algal solution (a concentration of algae in the concentrated algal solution) can be gradually increased as the concentrated algal solution moves from the one end side 312c to the other end side 312d.

Also, an algal solution need not necessarily be sprayed in a direction from the one end side 312c toward the other end side 312d as long as a spray direction thereof is a direction intersecting a plane direction of at least part of a front face of a main body. For example, as shown in FIG. 5B, the algae separating device 100B may adopt a spraying device 320 configured to spray an algal solution in a direction which is perpendicular to a plane direction of at least part of the front face 312a of the main body 312 (when a main body has a curved surface shape, one normal direction of the main body). Thus, the water removal efficiency of an algal solution (efficiency of removing a liquid from the algal solution) can be improved. To be specific, in a process in which the concentrated algal solution moves from part of the front face 312a onto which an algal solution is sprayed to the one end side 312c and the other end side 312d, a liquid is gradually removed from the concentrated algal solution from the front face 312a of the screen 310 toward the back face 312b thereof through the plurality of slits 314. Thus, a degree of concentration of the concentrated algal solution (a concentration of algae in the concentrated algal solution) can be gradually increased as the concentrated algal solution moves from part of the front face 312a to the one end side 312c and the other end side 312d.

As shown in FIG. 5C, the algae separating device 100C may adopt a screen 410 including a main body 412 having a front face 412a arranged to face upward in a vertical direction (a Z axis direction of FIG. 5) and a convex section 415 protruding from at least a part of the front face 412a upward in the vertical direction. In this case, the spraying device 320 may spray an algal solution toward the convex section 415. Thus, the concentrated algal solution can be concentrated on the front face 412a located in the vicinity of the convex section 415 and thus the concentrated algal solution can be easily collected. To be specific, in a process in which the concentrated algal solution moves from the convex section 415 onto which an algal solution is sprayed to the front face 412a located in the vicinity of the convex section 415, a liquid is gradually removed from the concentrated algal solution from the front face 412a of a screen 410 toward a back face 412b thereof through a plurality of slits 414. Thus, a degree of concentration of the concentrated algal solution (a concentration of algae in the concentrated algal solution) can be gradually increased as the concentrated algal solution moves from the convex section 415 to the front face 412a located in the vicinity of the convex section 415.

Although the embodiment of the present disclosure has been described above with reference to the drawings, the present disclosure is not limited to the above-described embodiment. The forms, combinations, and the like of the constituent elements illustrated in the above-described embodiment are merely examples and can be variously changed on the basis of design requirements or the like without departing from the gist of the present disclosure.

For example, a case in which the screen 110 is constituted of stainless steel has been described as an example in the above-described embodiment. However, a screen is not limited to stainless steel as long as the screen is made of a metal. Furthermore, a front face of a screen may be coated to prevent corrosion of a main body.

In the above-described embodiment, a case in which the rectangular slits 114 are used as through holes provided in the main body 112 has been described as an example. However, shapes of such through holes are not limited to a rectangular shape. Moreover, sizes of such through holes may be set to a size less than a minimum particle size of algae (or a colony), but it is sufficient for a size of at least one of the through holes to be set to a size less than a minimum particle size of algae.

In the above-described embodiment, a case in which widths of all of the slits 114 are set to a size less than a minimum particle size of algae has been described as an example. However, a width of at least one of the slits 114 may be set to a size less than a minimum particle size of algae.

In the above-described embodiment, the main body 112 having a curved shape in which the front face 112a side is concave and the back face 112b side is a convex section has been described as an example. However, a shape of a main body is not limited to such a curved shape.

In the above-described embodiment, the spraying device 120 configured to suction an algal solution from the culture tank 10 has been described as an example. However, a spraying device may suction an algal solution from not only a culture tank but also other storage tanks configured to store an algal solution.

In the above-described embodiment, the drying device 150 configured to dry the concentrated algal solution using natural drying has been described as an example. However, a drying device is not limited to a drying device configured to dry the concentrated algal solution using natural drying. For example, a drying device may be a device configured to dry the concentrated algal solution using air drying. Furthermore, when the algae are *Botryococcus braunii*, carbon dioxide is required for culturing. For this reason, when algae requiring carbon dioxide such as *Botryococcus braunii* are cultivated, carbon dioxide may be acquired from a carbon dioxide exhaust facility of a power plant or the like. Therefore, a drying device may dry the concentrated algal solution using waste heat generated in a carbon dioxide exhaust facility of a power plant or the like (waste heat drying). When a drying device is a drying device configured to dry the concentrated algal solution using air drying or a drying device configured to dry the concentrated algal solution using waste heat, dry algae can be produced at low cost.

Also, the algae separating device according to the above-described embodiment may include a heating device configured to heat a screen to improve water removal efficiency in the concentrated algal solution. In this case, a heating device may heat a screen using waste heat generated in a carbon dioxide exhaust facility of a power plant or the like. With such a heating device, water removal efficiency in the concentrated algal solution can be improved at low cost.

Also, in the method for producing the dry algae according to the above-described embodiment, a process in which the concentration step S220 is performed once has been described as an example. However, the concentration step S220 may be performed a plurality of times. The concentration step S220 may be performed a plurality of times so that a drying time using the drying device 150 can be shortened and thus an amount of heat required for drying can be reduced.

Note that the number of instances the concentration step S220 or a size of the screen 110 (a length in a moving direction of the concentrated algal solution), that is, a desired value of moisture content of the concentrated algal solution may be determined in consideration of the performance of a drying device 150 (in the case of natural drying, a working area, a temperature, a wind speed, and the like; in the case of air drying, a wind speed or a temperature of wind; and in the case of waste heat, a temperature of waste heat).

In the algae separating device according to the above-described embodiment, the algae separating device 100 including the drying means 150 has been described as an example. However, the drying device 150 is not essential for the algae separating device 100. For example, if the moisture content of the concentrated algal solution can be set to a value less than a predetermined value (for example, 70%) using only the screen 110, algae can be processed into a fuel or the like without including a drying device.

In the algae separating device according to the above-described embodiment, as algae to be separated by the algae separating device 100, *Botryococcus braunii* has been described as an example. However, algae are not limited to *Botryococcus braunii*. For example, algae may be microalgae such as *Spirulina* and may be algae other than microalgae.

INDUSTRIAL APPLICABILITY

According to the present disclosure, algae can be separated out at low cost.

What is claimed is:
1. An algae separating device configured to separate algae, the algae separating device comprising:
   an algal solution in which algae are suspended;
   a metal screen including a main body and a plurality of through holes passing through the main body from a front face to a back face; and
   a spraying device configured to spray the algal solution toward the front face of the main body;
   wherein
   the main body has a curved shape in which the front face side thereof is concave,
   one end side of the main body close to the spraying device is arranged vertically above the other end side of the main body far from the spraying device, and
   the main body is provided with no portion of the main body formed vertically below the other end side of the main body
   wherein the spraying device sprays the algal solution in a direction intersecting a plane direction of at least part of the front face of the main body and from the one end side of the main body toward the other end side thereof.
2. The algae separating device according to claim 1, wherein the algae are *Botryococcus braunii*.
3. A method for producing dry algae which separates algae from an algal solution in which algae are suspended and produces the dry algae, the method for producing the dry algae comprising:
   a step of spraying the algal solution toward a front face of a main body of a metal screen by a spraying device, the metal screen having the main body and a plurality of through holes passing through the main body from the front face to a back face;
   wherein
   the main body has a curved shape in which the front face side thereof is concave,
   one end side of the main body close to the spraying device is arranged vertically above the other end side of the main body far from the spraying device, and
   the main body is provided with no portion of the main body formed vertically below the other end side of the main body
   wherein the spraying device sprays the algal solution in a direction intersecting a plane direction of at least part of the front face of the main body and from the one end side of the main body toward the other end side thereof.

4. The method for producing the dry algae according to claim 3, further comprising:
a step of drying the algal solution, from which part of a liquid is removed, obtained by performing the step of spraying the algal solution using one or more of natural drying, air drying, and waste heat.

* * * * *